(12) United States Patent
Schorzman et al.

(10) Patent No.: US 7,534,836 B2
(45) Date of Patent: May 19, 2009

(54) BIOMEDICAL DEVICES

(75) Inventors: Derek Schorzman, Pittsford, NY (US); Joseph C. Salamone, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 350 days.

(21) Appl. No.: 11/173,698

(22) Filed: Jul. 1, 2005

(65) Prior Publication Data

US 2007/0004886 A1 Jan. 4, 2007

(51) Int. Cl.
*C08F 114/18* (2006.01)

(52) U.S. Cl. ............... 525/326.2; 525/50; 525/292; 526/211; 526/242; 526/247; 526/251

(58) Field of Classification Search ........... 526/247, 526/251, 242, 211; 525/326.2, 292, 50
See application file for complete search history.

(56) References Cited

U.S. PATENT DOCUMENTS

| | | | |
|---|---|---|---|
| 3,114,778 A | 12/1963 | Fritz et al. | |
| 3,310,606 A | 3/1967 | Fritz et al. | |
| 3,326,984 A | 6/1967 | Anderson et al. | |
| 3,397,191 A | 8/1968 | Beckerbauer | |
| 3,408,429 A | 10/1968 | Wichterle | |
| 3,660,545 A | 5/1972 | Wichterle | |
| 4,113,224 A | 9/1978 | Clark et al. | |
| 4,197,266 A | 4/1980 | Clark et al. | |
| 4,440,918 A | 4/1984 | Rice et al. | |
| 4,510,301 A * | 4/1985 | Levy | 526/254 |
| 4,555,732 A | 11/1985 | Tuhro | |
| 4,585,306 A * | 4/1986 | Ohmori et al. | 385/145 |
| 4,954,587 A | 9/1990 | Mueller | |
| 4,990,582 A | 2/1991 | Salamone | |
| 4,996,275 A | 2/1991 | Ellis et al. | |
| 5,010,141 A | 4/1991 | Mueller | |
| 5,021,602 A | 6/1991 | Clement et al. | |
| 5,023,380 A | 6/1991 | Babb et al. | |
| 5,037,917 A | 8/1991 | Babb et al. | |
| 5,037,918 A | 8/1991 | Babb | |
| 5,037,919 A | 8/1991 | Clement et al. | |
| 5,066,746 A | 11/1991 | Clement et al. | |
| 5,079,319 A | 1/1992 | Mueller | |
| 5,091,500 A | 2/1992 | Lysenko et al. | |
| 5,159,036 A | 10/1992 | Babb | |

(Continued)

FOREIGN PATENT DOCUMENTS

EP 443986 A1 * 2/1991

(Continued)

OTHER PUBLICATIONS

Babb et al., Journal of Applied Polymer Science, vol. 69, pp. 2005-2012 (1998).*

(Continued)

*Primary Examiner*—Peter D. Mulcahy
*Assistant Examiner*—Henry Hu
(74) *Attorney, Agent, or Firm*—John E. Thomas

(57) ABSTRACT

Biomedical devices are provided herein which are formed from a polymerization product of a monomeric mixture comprising one or more monomers comprising one or more trifluorovinyl groups, e.g., a perfluorocyclobutane containing polymer.

14 Claims, 5 Drawing Sheets

U.S. PATENT DOCUMENTS

| | | | |
|---|---|---|---|
| 5,159,037 | A | 10/1992 | Clement et al. |
| 5,159,038 | A | 10/1992 | Babb et al. |
| 5,196,569 | A | 3/1993 | Hung |
| 5,198,513 | A | 3/1993 | Clement et al. |
| 5,210,265 | A | 5/1993 | Clement et al. |
| 5,225,515 | A | 7/1993 | Lysenko et al. |
| 5,246,782 | A * | 9/1993 | Kennedy et al. ............ 428/421 |
| 5,268,511 | A | 12/1993 | Farnham |
| 5,271,875 | A | 12/1993 | Appleton et al. |
| 5,313,003 | A | 5/1994 | Krüger et al. |
| 5,364,547 | A | 11/1994 | Babb et al. |
| 5,364,917 | A | 11/1994 | Babb et al. |
| 5,391,796 | A | 2/1995 | Farnham |
| 5,409,777 | A * | 4/1995 | Kennedy et al. ......... 428/411.1 |
| 5,426,164 | A | 6/1995 | Babb et al. |
| 5,730,922 | A * | 3/1998 | Babb et al. .................. 264/258 |
| 5,991,081 | A * | 11/1999 | Haaland et al. ............. 359/589 |
| 6,559,237 | B1 | 5/2003 | Mao et al. |
| 6,646,075 | B2 | 11/2003 | Mao et al. |
| 6,649,715 | B1 | 11/2003 | Smith et al. |
| 7,294,657 | B2 * | 11/2007 | Olson et al. .................. 522/180 |
| 2002/0007083 | A1 | 1/2002 | DesMarteau et al. |
| 2002/0065382 | A1 | 5/2002 | Mao et al. |
| 2007/0004863 | A1 * | 1/2007 | Mentak ...................... 525/193 |

FOREIGN PATENT DOCUMENTS

| | | |
|---|---|---|
| EP | 0443986 A1 | 8/1991 |
| JP | 2-269306 | 2/1990 |
| WO | WO-2007/005356 A1 * | 1/2007 |

OTHER PUBLICATIONS

Smith et al., Macromolecules, vol. 29, pp. 852-860 (1996).*

Babb et al., "Perfluorocyclobutane Aromatic Ether Polymers. III. Synthesis and Thermal Stability of a Thermoset Polymer Containing Triphenylphosphine Oxide", *Journal of Applied Polymer Science*, vol. 69, pp. 2005-2012 (1998).

Babb et al., "Perfluorocyclobutane Aromatic Ether Polymers", *Journal of Polymer Science: Part A: Polymer Chemistry*, vol. 31, pp. 3465-3477 (1993).

Babb et al., "Perfluorocyclobutane Aromatic Ether Polymers", *Polymer. Prepr.*, 34(1), pp. 413-414 (1993).

Boone et al., "A New Aromatic Perfluorocyclobutane Polymer: Synthesis and Thermal Characterization of 1,3,5-Tris[(4-trifluorovinyloxy)phenyl]benzene", *Polymer. Prepr.*, 39(2), pp. 812-813 (1998).

Brandwood et al., J. Fluorine Chem. vol. 6, pp. 37-57 (1975).

Choi et al., "Synthesis and polymerization of trifluorovinylether-terminated imide oligomers I", *Polymer* 41, pp. 6213-6221 (2000).

Haken, "Studies in Trans-Esterification IV", *J. Appl. Chem.*, vol. 16 (March), p. 89 (1966).

Jasper et al., "New Monomers and Polymers Based on Trifluorovinyl Ether Functionalized Organosilanes, Siloxanes and Aminosilanes", Book of Abstracts, 215th ACS National Meeting, Dallas, Mar. 29-Apr. 2 (1998), 425.

Sarathy et al., "Hydrosilation Polymerization and Thermal Cure of Divinyl Trifluorovinyl Ether Monomers", *Polymer. Prepr.*, 39(1), pp. 609-610 (1998).

Shah et al., "Perfluorocyclobutane (PFCB) Polymers for Optical Fibers and Dielectric Waveguides", *Polymer. Prepr.*, 40(2), pp. 1293-1294 (1999).

Smith et al., "Crystalline Perfluorocyclobutane Polymers Containing the Hexafluoroisopropylidine Group", *Polymer Preprints*, vol. 41(1), pp. 60-61 (2000).

Smith et al., "Perfluorocyclobutyl Liquid Crystalline Fluoropolymers. Synthesis and Thermal Cyclopolymerization of Bis (trifluorovinyloxy)α-methylstilbene", *Macromolecules*, vol. 33 No. 4, pp. 1126-1128 (2000).

Smith et al., "Perfluorocyclobutane Aromatic Polyethers. Synthesis and Characterization of New Siloxane-Containing Fluoropolymers", *Macromolecules*, vol. 29, pp. 852-860 (1996).

Smith et al., "Fluorosilicones Containing the Perfluorocyclobutane Aromatic Ether Linkage", ACS Symposium Series (2000), 729 (Silicaones and Silicone-Modified Materials), Chapter 20, pp. 308-321.

Souzy et al., "Synthesis and (co)polymerization of monofluoro, difluoro, trifluorostyrene and ((trifluorovinyl)oxy)benzene", *Prog. Polym. Sci.*, vol. 29, pp. 75-106 (2004).

Topping et al., "Toward Crown Ether Containing Semifluoroinated Polyarylene Amides for Lithium Battery Membranes", *Polymer Preprints*, 43(1), pp. 486-487 (2002).

Wong et al., "Highly Fluorinated Trifluorovinyl Aryl Ether Monomers and Perfluorocyclobutane Aromatic Ether Polymers for Optical Waveguide Applications", *Macromolecules*, vol. 36, pp. 8001-8007 (2003).

Yuan et al., "Insights into the Properties of Novel Trifluorovinyl Ether Copolymers", *Macromolecules*, vol. 32, pp. 2669-2674 (1999).

Yuan et al., "Surface Enrichment of Poly(trifluorovinyl ether)s in Polystyrene Blends", *Macromolecules*, vol. 33, pp. 4926-4931 (2000).

Ji, et al., "[p-((Trifluorovinyl)oxy)phenyl]lithium: Formation, Synthetic Utility and Theoretical Support for a Versatile New Reagent in Fluoropolymer Chemistry" *Organometallics*, vol. 17, pp. 783-785 (1998).

Jin et al., "Synthesis and Characterization of Phenylphosphine Oxide Containing Perfluorocyclobutyl Aromatic Ether Polymers for Potential Space Applications", *Macromolecules*, vol. 36, pp. 9000-9004 (2003).

Kang, et al., "A Hyperbranched Aromatic Fluoropolyester for Photonic Applications", *Macromolecules*, vol. 36, pp. 4355-4359 (2003).

Kennedy et al., "Perfluorocyclobutane Aromatic Ether Polymers. II. Thermal/Oxidative Stability and Decomposition of a Thermoset Polymer", *Journal of Polymer Science: Part A: Polymer Chemistry*, vol. 33, pp. 1859-1865 (1995).

Kumar et al., "Synthesis and Polymerization of 1,1,1-tris(4-trifluorovinyloxyphenyl)2,2,2-trifluoroethane. A New Low Loss Optical Polymer", *Polymer Preprints*, vol. 42(2), pp. 500-501 (2001).

Ligon et al., "First separation of characterization of *cis* and *trans* 1,2-bisaryloxy perfluorocyclobutanes", *Journal of Fluorine Chemistry*, vol. 123, pp. 139-146 (2003).

Liou et al., "The Effect of Crosslinking on Thermal and Mechanical Properties of Perfluorocyclobutane Aromatic Ether Polymers", *Journal of Polymer Science: Part B: Polymer Chemistry*, vol. 36, pp. 1383-1392 (1998).

Lousenberg et al., "Synthesis of Trifluorovinyl Ethane Incorporating Functionalized Hydrocarbon Ether Groups: Insight into the Mechanism of Trifluorovinyl Ether Formation from Trimethylsilyl 2-alkoxy-2,3,3,3,-tetrafluoropropionates", *J. Org. Chem.*, vol. 62, pp. 7844-7849 (1997).

Ma et al., "Novel Class of High-Performance Perfluorocyclobutane-Containing Polymers for Second-Order Nonlinear Optics", *Chem. Mater.*, vol. 12, pp. 1187-1189 (2000).

Mellon et al., "Kinetics and Radical Characterization of Aryl Trifluorovinyl Ether Polymerization Using ESR Spectroscopy", *Polymer Preprints*, vol. 44(1), pp. 1181-1182 (2003).

Rizzo et al., "Perfluorocyclobutane-containing silarylene-siloxane polymers with pendant trifluoropropyl groups", *Polymer. Prepr.*, 40(2), pp. 874-875 (1999).

Rizzo et al., "Preparation of Trifluorovinylether-terminated fluorosilicone oligomers" Book of Abstracts, 217th ACS Meeting, Anaheim, CA, Mar. 21-25 (1999).

Rizzo et al., "Synthesis and thermal properties of fluorosilicaones containing perfluorocyclobutane rings", *Polymer 41*, pp. 5125-5136 (2000).

Sarathy et al., "Fluorosilicone Networks From Trifluorovinyl Ether Pendant Polysiloxanes", *Polymer. Prepr.*, 39(1), pp. 530-531 (1998).

* cited by examiner

BIOMEDICAL DEVICES

BACKGROUND OF THE INVENTION

1. Technical Field

The present invention generally relates to biomedical devices, and especially ophthalmic lenses that are intended for direct placement on or in the eye such as contact lenses or intraocular lenses, where the devices and lenses are obtained from the polymerization products of monomeric mixtures containing one or more trifluorovinyl monomers.

2. Description of Related Art

In the field of biomedical devices such as contact lenses, various factors must be considered in order to yield a material that has appropriate characteristics. For example, various physical and chemical properties such as oxygen permeability, wettability, material strength and stability are but a few of the factors that must be carefully balanced to provide a useable contact lens. Since the cornea receives its oxygen supply exclusively from contact with the atmosphere, good oxygen permeability is a critical characteristic for any contact lens material. Wettability is also important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

Contact lenses made from fluorinated materials have been investigated for a number of years. Such materials can generally be subdivided into two major classes, namely hydrogels and non-hydrogels. Hydrogels can absorb and retain water in an equilibrium state whereas non-hydrogels do not absorb appreciable amounts of water. Regardless of their water content, both hydrogel and non-hydrogel fluorinated contact lenses tend to have relatively hydrophobic, non-wettable surfaces.

By introducing fluorine-containing groups into contact lens polymers, the oxygen permeability can be significantly increased. For example, U.S. Pat. No. 4,996,275 discloses using a mixture of comonomers including the fluorinated compound bis(1,1,1,3,3,3-hexafluoro-2-propyl)itaconate in combination with organosiloxane components. Fluorinating certain polysiloxane materials has been indicated to reduce the accumulation of deposits on contact lenses made from such materials. See, for example, U.S. Pat. Nos. 4,440,918; 4,954,587; 4,990,582; 5,010,141 and 5,079,319. However, fluorinated polymers can suffer from one or more of the following drawbacks: difficult and/or expensive synthetic routes, poor processability, low refractive index, poor wettability, poor optical clarity, poor miscibility with other monomers/reagents and toxicity.

Perfluorocyclobutane polymerization products of trifluorovinyl-containing monomers, e.g., bis-trifluorovinyl monomers, are known. See, e.g., U.S. Pat. Nos. 5,021,602; 5,023,380; 5,037,917; 5,037,918; 5,037,919; 5,066,746; 5,159,036; 5,159,037; 5,159,038; 5,162,468; 5,198,513; 5,210,265; 5,246,782; 5,364,547; 5,364,917 and 5,409,777. U.S. Patent Application Publication No. 2002/0065382 discloses high molecular weight perfluorocyclobutane polymers obtained from the polymerization of trifluorovinyl monomers in the presence of a catalyst or initiator. U.S. Pat. Nos. 5,246,782 and 5,409,777 further disclose that the polymers are useful as, for example, passivation coatings on medical instruments and in packaging for medical devices such as bandages and operating equipment. However, there has been no recognition or appreciation that such materials can be employed in the manufacture of biomedical devices and particularly contact lens applications.

Accordingly, it would be desirable to provide improved biomedical devices formed from fluorinated polymerization products that exhibit suitable physical and chemical properties, e.g., oxygen permeability and wettability, for prolonged contact with the body while also being biocompatible.

SUMMARY OF THE INVENTION

In accordance with one embodiment of the present invention, a biomedical device is provided which is formed from a polymerization product of a monomeric mixture comprising one or more monomers comprising one or more trifluorovinyl groups.

In accordance with a second embodiment of the present invention, a biomedical device is provided which is formed from a polymerization product of a monomeric mixture comprising one or more monomers comprising one or more trifluorovinyl ether groups.

In accordance with a third embodiment of the present invention, a biomedical device is provided which is formed from a polymerization product of a monomeric mixture comprising one or more monomers comprising one or more trifluorovinyl aromatic ether groups.

In accordance with a fourth embodiment of the present invention, a contact lens is provided which comprises a polymerization product of a monomeric mixture comprising one or more monomers comprising one or more trifluorovinyl groups.

In accordance with a fifth embodiment of the present invention, a biomedical device is provided which is formed from a polymer or copolymer having a backbone comprising one or more perfluorocyclobutane groups.

In accordance with a sixth embodiment of the present invention, a contact lens is provided which comprises a polymer or copolymer having a backbone comprising one or more perfluorocyclobutane groups.

BRIEF DESCRIPTION OF THE DRAWINGS

The figures set forth herein illustrate various embodiments of the present invention wherein.

DETAILED DESCRIPTION OF THE PREFERRED EMBODIMENTS

Figure 1:
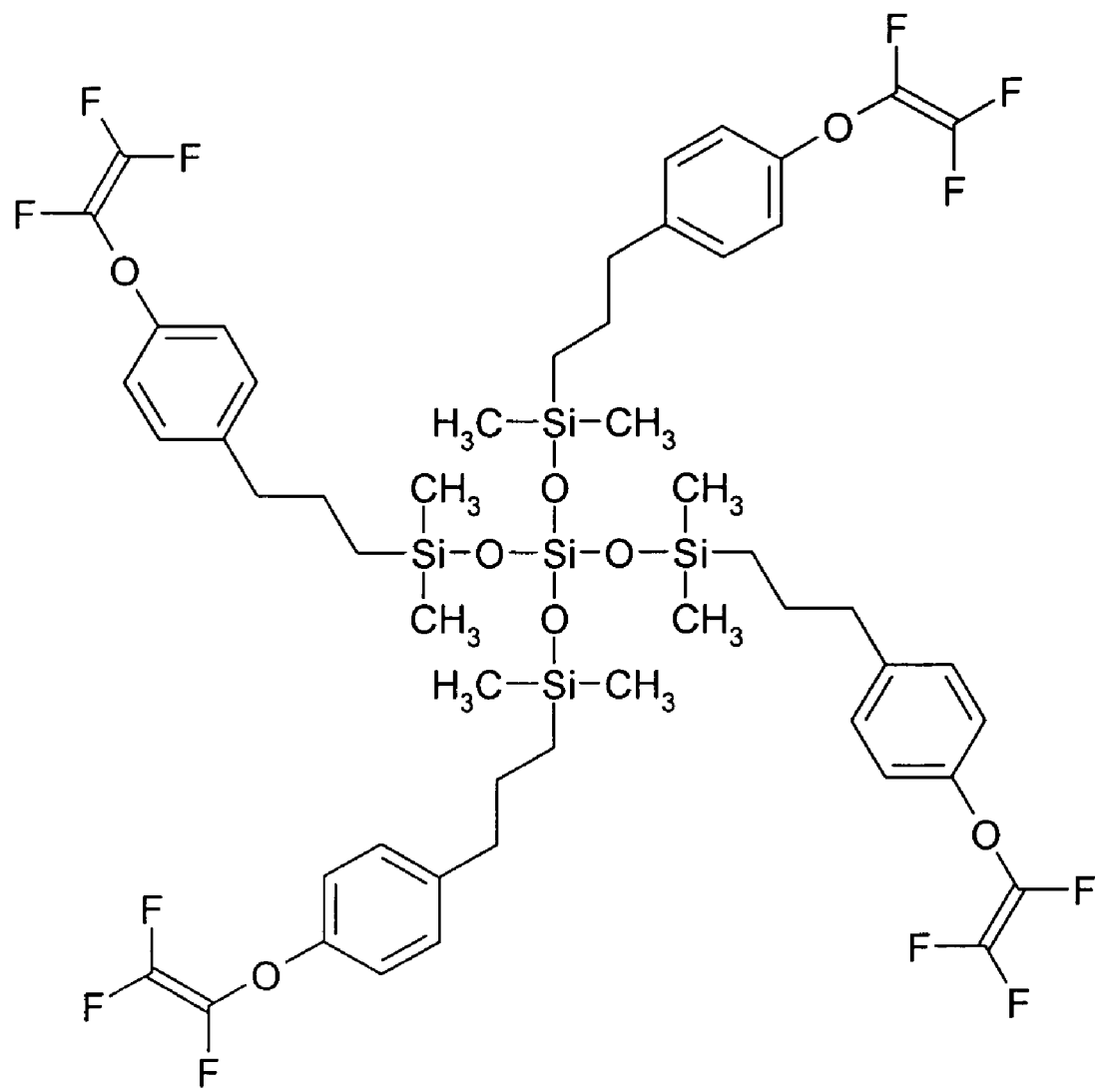
FIG. 1 is a polysiloxane containing star which can be employed in the manufacture of a biomedical device of the present invention.

The present invention is directed to biomedical devices intended for direct contact with body tissue or body fluid. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye such as, for example, intraocular devices and contact lenses. A wide variety of types of contact lens materials can be produced herein ranging from hard, gas permeable lens materials; soft, hydrogel lens materials; to soft, non-hydrogel lens materials. A particularly preferred contact lens is a rigid gas permeable lens.

The biomedical devices of the present invention are advantageously formed from a polymerization product of a monomeric mixture comprising one or more monomers comprising one or more trifluorovinyl groups, e.g., a polymer or copolymer having a backbone comprising one or more perfluorocyclobutane groups. The polymer or copolymer polymerization products can be obtained by the polymerization or copolymerization of one or more trifluorovinyl containing monomers. For example, the polymers or copolymers can be obtained by free radical polymerization of the one or more trifluorovinyl containing monomers to form biomedical devices according to conventional methods. Alternatively, the polymers or copolymers can be obtained by thermal polymerization of the one or more trifluorovinyl containing monomers to form biomedical devices according to conventional methods.

Suitable trifluorovinyl containing monomers useful in forming the polymers or copolymers include, but are not limited to, monomers having at least one or more trifluorovinyl groups, monomers having at least one or more trifluorovinyl ether groups, monomers having at least one or more trifluorovinyl aromatic ether groups, monomers having at least two dimerizable perfluorovinyl groups, monomers having at least two dimerizable perfluorovinyl ether groups, monomers having at least two dimerizable perfluorovinyl aromatic ether groups and the like and combinations thereof.

In one embodiment, the monomeric mixture will include at least one or more trifluorovinyl containing monomers represented by the general formula I:

$$R^1-(X-CF=CF_2)_z \quad (I)$$

wherein $R^1$ represents one or more inertly substituted groups, X is independently a group which links the inertly substituted groups and the trifluorovinyl group and z is from 1 to about 1000, preferably from 1 to about 100, more preferably from 1 to about 10 and most preferably from 1 to about 6. As one skilled in the art would readily appreciate, the trifluorovinyl containing moiety can be present as one or more pendant groups in the monomer, e.g., in the case where $R^1$ is an alkylene group such as ethylene or in the case where $R^1$ is a polycyclic group, as well as an end group(s). The X groups can be the same or different and include, but are not limited to, a bond, an oxygen atom, a sulfur atom, a carboxylic or thiocarboxylic ester group, an amide group, a sulfone, a sulfoxide, a carbonate, a carbamate, a perfluoroalkylene, a perfluoroalkylene ether, an alkylene, an acetylene, a phosphine, a carbonyl or thio carbonyl group; seleno; telluro; nitrido; a silanediyl group, a trisilanediyl group, a tetrasilanetetrayl group, a siloxanediyl group, a disiloxanediyl group, a trisiloxyldiyl group, a trisilazanyl group, a silythio group, a boranediyl group; and the like and combinations thereof. By "inert" it is meant that the structures or substituents do not react undesirably with the perfluorovinyl groups or interfere undesirably with polymerization (e.g., perfluorocyclobutane formation) of the monomers.

Representative $R^1$ groups include, by way of example, a substituted or unsubstituted $C_1$ to $C_{30}$ hydrocarbyl group such as a substituted or unsubstituted $C_1$ to $C_{30}$ and preferably a substituted or unsubstituted $C_1$ to $C_{16}$ alkyl or an aromatic group optionally containing one or more heteroatoms; or $C_3$-$C_{25}$ cycloalkyl groups optionally containing one or more heteroatoms. In one embodiment, $R^1$ comprises one or more substituted or unsubstituted cyclic or polycyclic containing groups, e.g., one or more substituted or unsubstituted aromatic groups optionally containing one or more heteroatoms. Suitable aromatic group(s) can be of any molecular structure having aromatic character such as at least one six membered aromatic ring, optionally having any number of such six-membered rings fused together or connected by bonds or linking structures. For example, the aromatic groups can have from 1 to about 50 such substituted or unsubstituted aromatic rings, and preferably from 1 to about 10 substituted or unsubstituted aromatic rings. If desired, when more than one cyclic containing group such as the aromatic groups are employed, the cyclic containing groups can be linked together with the same or different linking group, e.g., a $C_1$-$C_{20}$ alkylene or haloalkylene group optionally containing ether or ester linkages.

Examples of aromatic groups for use herein include, but are not limited to, the following structures:

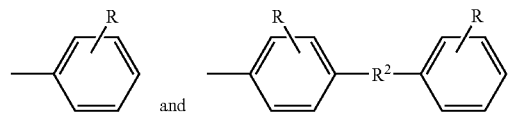

wherein R is independently hydrogen, a $C_1$-$C_{20}$ alkyl group, a hydroxyl group, a $C_1$-$C_{20}$ carboxylic acid group, a $C_1$-$C_{20}$ ester group, a $C_1$-$C_{20}$ alkoxy group, $CO_2^-$, $SO_3^-$, $PO_3^-$, $OPO_3^{2-}$, F, Br, I, $NA_2$ or $NA_3^+$ wherein A is independently hydrogen, a $C_1$-$C_{20}$ alkyl group, a hydroxyl group, a $C_1$-$C_{20}$ carboxylic acid group, a $C_1$-$C_{20}$ ester group, or a $C_1$-$C_{20}$ alkoxy group, or two R groups together with the carbon atom to which they are bonded are joined together to form a cyclic structure optionally containing one or more heterocyclic groups; and $R^2$ is a bond, a $C_1$-$C_{20}$ alkylene or haloalkylene group optionally containing ether or ester linkages. Representative examples of such aromatic groups include, but are not limited to,

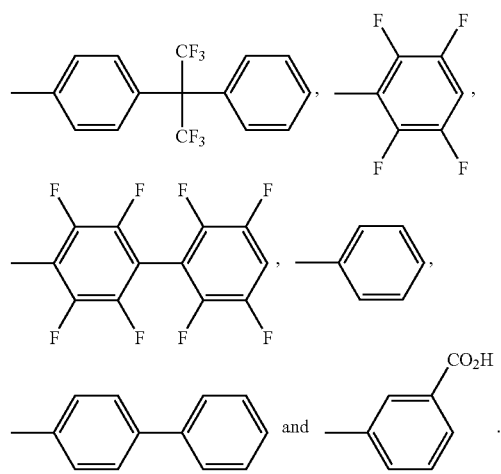

Although the aromatic groups of $R^1$ are shown as being bonded in the para position, all positions on the aromatic ring are contemplated herein, e.g., ortho, meta, para and combinations thereof. In another embodiment, $R^1$ comprises one or more substituted or unsubstituted cyclic or polycyclic siloxane containing groups.

In an alternative embodiment, the monomeric mixture will include at least one or more trifluorovinyl containing monomers represented by the general formula II:

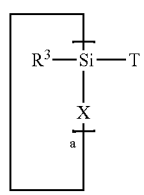

wherein X has the aforestated meaning; $R^3$ is independently hydrogen, a substituted or unsubstituted $C_1$-$C_{30}$ alkyl, a substituted or unsubstituted $C_1$-$C_{30}$ alkoxy, a substituted or unsubstituted $C_3$-$C_{30}$ cycloalkyl, a substituted or unsubstituted $C_3$-$C_{30}$ cycloalkylalkyl, a substituted or unsubstituted $C_3$-$C_{30}$ cycloalkenyl, a substituted or unsubstituted $C_5$-$C_{30}$ aryl, a substituted or unsubstituted a $C_5$-$C_{30}$ arylalkyl, a substituted or unsubstituted $C_5$-$C_{30}$ heteroaryl, a substituted or unsubstituted $C_3$-$C_{30}$ heterocyclic ring, a substituted or unsubstituted $C_4$-$C_{30}$ heterocycloalkyl, or a substituted or unsubstituted $C_6$-$C_{30}$ heteroarylalkyl; a is from 1 to about 100 and preferably from 1 to about 10; and T is the same or different and is of the general formula:

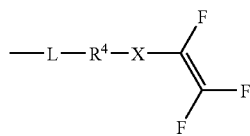

wherein $R^4$ independently represents one or more inertly substituted groups as defined above for $R^1$; X independently is a group which links the inertly substituted groups and the trifluorovinyl group and has the aforestated meanings and L is an optional linking group and independently is a straight or branched $C_1$-$C_{30}$ alkyl group, a $C_3$-to $C_{30}$ cycloalkyl group, a $C_5$-$C_{30}$ aryl group, an ether group, a $C_1$-$C_{20}$ ester group, an amide group, a siloxanyl, an arylsiloxanyl or a fluorosiloxanyl. Specific examples of the foregoing trifluorovinyl containing monomers of formula II are set forth in FIGS. 1-3.

The foregoing trifluorovinyl containing monomers are either commercially available from such sources as, for example, Tetramer Technologies through Oakwood Products (West Columbia, S.C.), or can be prepared by any method known in the art which links molecular structures having perfluorovinyl groups to other molecular structures or which form perfluorovinyl groups and does not constitute a part of the present invention. See, e.g., U.S. Pat. No. 5,023,380.

The monomeric mixtures containing the foregoing trifluorovinyl containing monomers may be polymerized by free radical polymerization by exposing the mixture to heat and/or radiation, e.g., ultraviolet light (UV), visible light, or high energy radiation, to produce biomedical devices such as contact lenses according to conventional methods. A polymerization initiator may be included in the mixture to facilitate the polymerization step. Representative free radical thermal polymerization initiators are organic peroxides such as, for example, acetal peroxide, lauroyl peroxide, decanoyl peroxide, stearoyl peroxide, benzoyl peroxide, tertiarylbutyl peroxypivalate, peroxydicarbonate, and the like and mixtures thereof. Representative UV initiators are those known in the field such as, for example, benzoin methyl ether, benzoin ethyl ether, Darocure 1173, 1164, 2273, 1116, 2959, 3331 (EM Industries) and Igracure 651 and 184 (Ciba-Geigy), and the like and mixtures thereof. Generally, the initiator will be employed in the monomeric mixture at a concentration at about 0.1 to about 5 percent by weight of the total mixture.

When producing polymers and copolymers from the free radical polymerization process, the polymers and copolymers, for the case of the trifluorovinyl containing monomers of formula I wherein z is 1,will ordinarily have repeating units of the general formula:

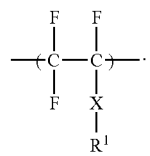

It is to be understood that the number of perfluoroaliphatic groups can vary from as few as one up to thousands. For the trifluorovinyl containing monomers of formula I wherein z is 2,the polymers and copolymers produced by the free radical polymerization method will ordinarily have repeating units of the general formula:

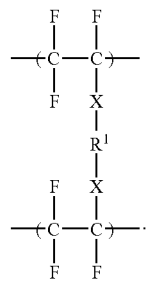

As with the polymers or copolymers produced from the monomer of formula I wherein z is 1,the number of perfluoroaliphatic groups can vary from as few as one up to thousands. For the trifluorovinyl containing monomers of formula I wherein z is 1 to 6 or more, the polymers and copolymers produced from the free radical polymerization method will result in a highly crosslinked polymer system. Additionally, similar repeating units will form when polymerizing the monomers represented in formula II.

In another embodiment of the present invention, one or more trifluorovinyl containing monomers having at least two dimerizable perfluorovinyl groups can be polymerized to provide the biomedical devices of the present invention. A dimerizable perfluorovinyl group is a perfluorovinyl group which reacts with another such group to form one or more perfluorocyclobutane rings represented by the general formula:

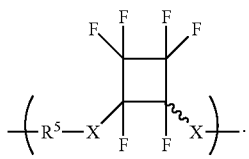

Thus, the resulting polymers will have one or more perfluorocyclobutane groups, and includes oligomers which have from about 2 to about 100 repeating units. The molecular weight of the resulting polymers can vary widely, e.g., a number average molecular weight of at least about 100 and can range from about 100 to about 1,000,000. It is to be understood that depending on the molecular structure connecting the perfluorocyclobutane groups, the number of perfluorocyclobutane groups can vary from as few as one up to thousands. The process of forming polymers or oligomers herein is general and capable of forming biomedical devices having wide ranges of utility. The physical and chemical properties of the resulting products are highly dependent on the choice of the molecular structure between the perfluorocyclobutane groups as well as the number of perfluorocyclobutane groups.

Any monomer having at least two dimerizable perfluorovinyl groups can be used herein. Whereas polyaddition of perfluorovinyl groups to form perfluoroaliphatic polymers (like polytetrafluoroethylene), not generally having perfluorocyclobutane groups, takes place in the presence of free radicals or free radical generating catalysts, dimerization to form perfluorocyclobutane groups takes place thermally.

When a perfluorovinyl group is dimerizable, dimerization is preferably favored over other thermal reactions either kinetically or in equilibrium. As one skilled in the art would readily appreciate, the perfluorovinyl groups on a monomer can be separated by at least one atom or group of atoms which does not facilitate isomerization. The atom or group of atoms can include at least one aromatic group or can include an aliphatic or cycloalkyl group. However, aromatic groups are usually preferred due their ease of manufacturing monomers. Furthermore, when the perfluorovinyl groups are attached to aliphatic carbons or separated from aliphatic carbons by single atoms such as, for example, oxygen, the perfluorovinyl groups are preferably primary or secondary because tertiary perfluorovinyl groups are generally sterically hindered with respect to formation of perfluorocyclobutane rings, and more preferably the perfluorovinyl groups are primary because secondary perfluorovinyl groups tend to rearrange. Preferably, to avoid rearrangement and facilitate polymer formation the monomers have structures such that the resulting polymers have hydrocarbyl groups, e.g., a substituted or unsubstituted cyclic or polycyclic containing group, perfluorocyclobutane groups and at least one non-carbon atom, e.g., oxygen, silicon, boron, phosphorus, nitrogen, selenium, germanium, tellurium and/or sulfur atom (each optionally substituted) in the backbones.

In one embodiment, the monomeric mixture will include at least one or more trifluorovinyl containing monomers having at least two dimerizable perfluorovinyl groups represented by the general formula III:

$$F_2C=CF-X-R^5-(X-CF=CF_2)_m \tag{III}$$

wherein $R^5$ represents one or more inertly substituted groups as defined above for $R^1$; X independently is a group which links the inertly substituted groups and the trifluorovinyl group and has the aforestated meanings; and m is an integer of 1 to about 1000, preferably from 1 to about 100, more preferably from 1 to about 10 and most preferably from 1 to about 5. In an alternative embodiment, the monomeric mixture will include at least one or more trifluorovinyl containing monomers having at least two dimerizable perfluorovinyl groups as represented by the general formula II above, i.e., the case wherein a is from 2 to about 100 and preferably from 2 to about 10.

The foregoing monomers having at least two dimerizable perfluorovinyl groups useful in the practice of the invention are commercially available from such sources as, for example, Tetramer Technologies through Oakwood Products (West Columbia, S.C.), or can be prepared by any method known in the art which links molecular structures having perfluorovinyl groups to other molecular structures or which form perfluorovinyl groups as discussed above and does not constitute a part of the present invention.

In another embodiment, the monomeric mixture will include at least one or more trifluorovinyl containing monomers having at least two dimerizable perfluorovinyl groups represented by the general formula IV:

$$F_2C=CF-X-R^6-(X-CF=CF_2)_m \tag{IV}$$

wherein each X has the aforestated meaning and is independently a group which links the $R^6$ group and the trifluorovinyl group; $R^6$ is one or more substituted or unsubstituted $C_3$-$C_{25}$ cycloalkyl groups optionally containing one or more heteroatoms and when more than one cycloalkyl group are employed, the cycloalkyl groups can be linked together with the same or different linking group, e.g., a $C_1$-$C_{20}$ alkylene or haloalkylene group optionally containing ether or ester linkages, and m has the aforestated meanings. Representative examples of such cycloalkyl groups are of the formulae

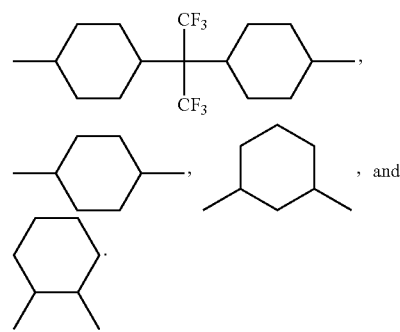

The monomeric mixtures containing the trifluorovinyl containing monomers having at least two dimerizable perfluorovinyl groups can be polymerized by heating the monomeric mixture to a temperature and for a time sufficient to form a polymer or copolymer having one or more perfluorocyclobutane rings in the backbone of the polymer. Suitable temperatures for forming one or more perfluorocyclobutane rings can differ according to the structure of the monomer. In general, temperatures can range from about 50° C. to about 400° C. and preferably from about 75° C. to about 300° C. for formation of perfluorocyclobutane rings. Temperatures above about 450° C. are usually avoided because perfluorocyclobutane groups are generally thermally unstable above such temperatures. In another embodiment, a temperature of from about 100° C. to about 230° C. is generally most preferred for cyclization of perfluorovinyl aromatic or aliphatic ethers or sulfides, while a temperature of from about 50° C. to 80° C. is needed to form perfluorocyclobutane groups when the perfluorovinyl group is attached directly to an aromatic ring. A suitable time can vary according to the temperature used and the structure of the monomer. Generally, the time period for the polymerization can range from about 1 hour to about 100 hours and preferably from about 10 hours to about 40 hours. Polymerization can take place in one stage or in multi-stages.

When the trifluorovinyl containing monomers are capable of radical initiated addition polymerization, conditions conducive to free radical polymerization, e.g. presence of oxygen, ozone, peroxygen compounds and other free radical generating compounds, are avoided so that the trifluorovinyl groups will dimerize into perfluorocyclobutane groups rather than undergoing addition polymerization. Compounds known in the art for stabilization against free radical polymerization are alternatively used. Similarly, when the trifluorovinyl groups are capable of addition polymerization in the presence of anions or cations, compounds which supply such anions or cations are avoided. For example, fluoride ions (e.g. from carbonyl fluorides), chloride, hydroxide, phenoxide and the like are avoided. To avoid such compounds as carbonyl fluorides, oxidative conditions such as the presence of oxygen, hypochlorite, dichromate, permanganate and the like are avoided because the perfluorovinyl groups are known to oxidize to form carbonyl fluorides. Perfluorovinyl ethers, thioethers, sulfones, sulfoxides and the like are relatively stable with regard to addition polymerization and oxidation; and, therefore, such precautions are generally unnecessary when such perfluorovinyl compounds are used.

The monomeric mixtures are suitably neat or, optionally, in admixture with other materials such as in a solution, an emulsion, in supercritical carbon dioxide, a dispersion or in any other form in which monomer molecules can be contacted with one another to form a polymer.

Suitable solvents are those which are inert to the conditions encountered in the polymerization reaction and include, but are not limited to, xylene, mesitylene and perfluorotetradecahydrophenanthrene. At atmospheric pressure, preferred solvents are those which attain temperatures of about 170° C. to about 250° C. such as, for example, dichlorobenzene, trichlorobenzene, diphenyl oxide and perfluorotetradecahydrophenanthrene. When a solvent is used, the concentration of monomers in solvent is advantageously from about 0.1 to about 99.9 weight percent and preferably from about 10 to about 90 weight percent by weight monomer.

Polymerization or dimerization suitably takes place at any pressure. Pressures are generally chosen such that the monomers and any solvents and/or dispersing media remain liquid at the temperatures used for polymerization. When the monomers or other materials evaporate at temperatures used, then it is generally preferable to maintain a pressure at least sufficient to maintain the materials liquid.

The biomedical devices of the present invention, e.g., contact lenses or intraocular lenses, can be prepared by polymerizing the foregoing trifluorovinyl containing monomers to form a product that can be subsequently formed into the appropriate shape by, for example, lathing, injection molding, compression molding, cutting and the like. Alternatively, the reaction mixture may be placed in a mold and subsequently cured into the appropriate product.

For example, in producing contact lenses, the initial monomeric mixture containing the foregoing trifluorovinyl containing monomers, e.g., the trifluorovinyl containing monomers of formulae I-IV, may be polymerized in tubes to provide rod-shaped articles, which are then cut into buttons. The buttons may then be lathed into contact lenses. Alternately, the contact lenses may be cast directly in molds from the monomeric mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the monomer mixture to a mold, and spinning the mold in a controlled manner while exposing the monomer mixture to a radiation source such as UV light. Static casting methods involve charging the monomeric mixture between two mold sections, one mold section shaped to form the anterior lens surface and the other mold section shaped to form the posterior lens surface, and curing the monomeric mixture while retained in the mold assembly to form a lens, for example, by free radical polymerization of the monomeric mixture. Examples of free radical reaction techniques to cure the lens material include thermal radiation, infrared radiation, electron beam radiation, gammma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a monomeric mixture is cured by spincasting in a mold to form a shaped article having an anterior lens surface and a relatively large thickness, and the posterior surface of the cured spincast article is subsequently lathed to provide a contact lens having the desired thickness and posterior lens surface.

When polymerizing the monomeric mixture by the thermal technique discussed above, a polymeric resin or metal material that is capable of withstanding high temperatures, i.e., thermally stable, should be employed as a contact lens mold. For example, in injection molding, the resin should have a heat deflection temperature of at least 350° C. and a hardness of at least 100 on the Rockwell Hardness Scale (M scale). Suitable resins include, but are not limited to, engineering plastics based on polyetherimide resins (e.g., ULTEM™ available from General Electric Co., Polymers Product Dept.); polyamide-imide plastics (e.g., TORLON available from Amoco Performance Products); polyphenylene sulfide plastics (e.g., RYTON™ available from Phillips Petroleum Co.); polysulfone and polyarylsulfone plastics (e.g., UDELT™ and RADEL™ available from Amoco Performance Products); polythalamide plastics (e.g., AMODEL available from Amoco Performance Products); polyketone plastics (e.g., KADEL™ available from Amoco Performance Products); various liquid crystal polymer resins (e.g., XYDAR™ available from Amoco Performance Products) and the like.

Optionally, the monomeric mixtures herein may include additional components according to the specific type of lens being produced. For example, when producing rigid gas-permeable (RGP) materials, the monomeric mixture may include in addition to the foregoing trifluorovinyl containing monomers, one or more crosslinking agents, a small amount of a wetting monomer; and optionally other agents such as strengthening agents or UV absorbing or dye monomers. The crosslinking and wetting agents can include those crosslinking and wetting agents known in the prior art for making RGP materials. The content of the crosslinking agent is chosen to provide a dimensionally stable lens material resistant to breakage and stress crazing. The amount of wetting monomer used is adjusted within limits to provide sufficient wetting characteristics so as to maintain a stable tear film while at the same time keeping a sufficiently low water content, e.g., a polymer system containing less than about 5 wt. % water.

When producing a hydrogel lens, the monomeric mixture may include in addition to, the foregoing trifluorovinyl containing monomers, at least a diluent that is ultimately replaced with water when the polymerization product is hydrated to form a hydrogel. Generally, the water content of the hydrogel is greater than about 5 wt. % and more commonly between about 10 to about 80 wt. %. The amount of diluent used should be less than about 50 wt. % and in most cases, the diluent content will be less than about 30 wt. %. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; and the like and mixtures thereof. If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired the monomeric mixture used to produce the hydrogel lens may further include crosslinking and wetting agents known in the prior art for making hydrogel materials.

The contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative of the invention. The examples should not be read as limiting the scope of the invention as defined in the claims. Various homopolymers and copolymers films were formed and characterized by standard testing procedures such as:

1. Modulus ($g/mm^2$) and elongation were measured per ASTM 1708 employing an Instron (Model 4502) instrument where the film sample was immersed in borate buffered saline; an appropriate size of the film sample was gauge length 22 mm and width 4.75 mm, where the sample further has ends forming a dogbone shape to accommodate gripping of the sample with clamps of the Instron instrument, and a thickness of 200±50 microns.
2. Tensile strength ($g/mm^2$) was measured per ASTM test method D1708a.
3. Oxygen permeabilities (also referred to as Dk) were determined by the following procedure. Other methods and/or instruments may be used as long as the oxygen permeability values obtained therefrom are equivalent to the described method. The oxygen permeability of the films were measured by the polarographic method (ANSI Z80.20-1998) using an O2 Permeometer Model 201T instrument (Createch, Albany, Calif. USA) having a probe containing a central, circular gold cathode at its end and a silver anode insulated from the cathode. Measurements are taken only on pre-inspected pinhole-free, flat film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone films, it is frequently useful to employ a Teflon polymer membrane, e.g., having a circular disk shape, between the probe cathode and the film sample. In such cases, the Teflon membrane is first placed on the premoistened cathode, and then the film sample is placed on the Teflon membrane, ensuring no air bubbles or excess PBS exists beneath the Teflon membrane or film sample. Once measurements are collected, only data with correlation coefficient value ($R^2$) of 0.97 or higher should be entered into the calculation of Dk value. At least two Dk measurements per thickness, and meeting $R^2$ value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a +/−8.8% of the Repository values established by William J. Benjamin, et al., *The Oxygen Permeability of Reference Materials*,Optom Vis Sci 7 (12s): 95 (1997), the disclosure of which is incorporated herein in its entirety:

| MATERIAL NAME | Repository Values | Lower Limit | Upper Limit |
|---|---|---|---|
| Fluoroperm 30 | 26.2 | 24 | 29 |
| Menicon EX | 62.4 | 56 | 66 |
| Quantum II | 92.9 | 85 | 101 |

Figure 4:
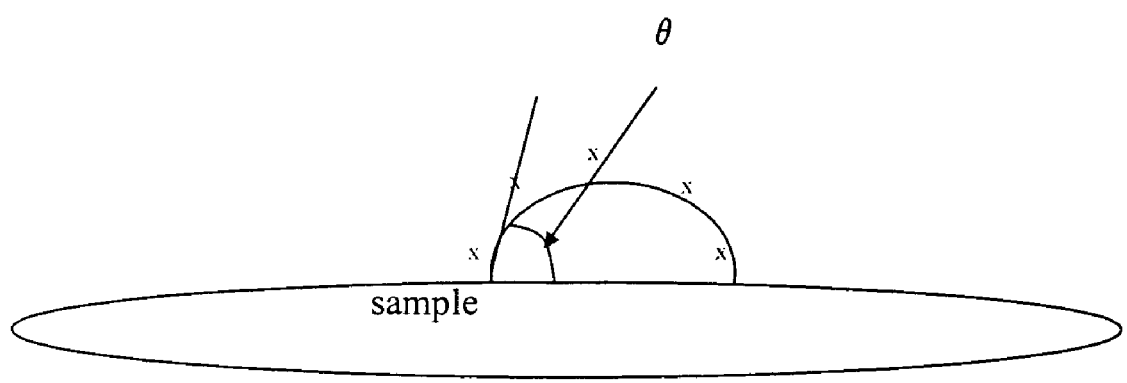
FIG. 4 illustrates a contact angle ($\theta$) shown for the left side of the drop for measuring the Static Contact Angle (SCA) of Examples 7-9.

4. Refractive index was measured per typical methods on hydrated samples using a refractometer.
5. Static Contact Angle (SCA)—The instrument used for this measurement was an AST Products Video Contact Angle System (VCA) 2500XE. This instrument utilizes a low-power microscope that produces a sharply defined image of the water drop, which is captured immediately on the computer screen. Surface Tension of the water used for analysis was periodically measured by the dynamic contact angle method and averaged 73 dynes/cm. The water was 80 µl drawn into the VCA system microsyringe, and 0.6 µl drops were dispensed from the syringe onto the sample. The contact angle is calculated by placing five markers along the circumference of the drop as shown below. The software generated a curve representing the circumference of the drop and calculated the contact angle of the drop with respect to the surface on both sides of the drop. The contact angle (θ) as shown for the left side of the drop is generally set forth in FIG. 4. All films were received in water, and soaked in HPLC water for 15 minuntes prior to analysis. Sections of the films were placed onto a clean glass slide and allowed to dry overnight in a nitrogen dry box. Five drops of water were used to measure the contact angle of each sample.

In the following examples, the properties of such films derived from the claimed prepolymer and combinations of prepolymers with various comonomers are described.

EXAMPLE 1

This example illustrates the preparation of a 3-(4-[trifluorovinyloxy]phenyl)propyl terminated poly(dimethylsiloxane) having a number average molecular weight ($M_n$) of 1523 and a polydispersity (PD) of 1.35 (as determined using SEC and by comparison to standards of known molecular weight) and of the formula

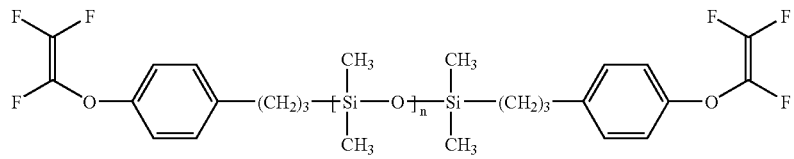

wherein n is an average of 8.

To a solution of hydride terminated poly(dimethylsiloxane) obtained from Aldrich Chemical Co. (Milwaukee, Wis.) (average $M_n$ 580 g/mol, 3.47 g) and 4-(trifluorovinyloxy)allylbenzene (3.87 g, 17.9 mmol) prepared from 1-bromo-4-(trifluorovinyloxy)benzene obtained from Oakwood Products, Inc. (West Columbia, S.C.) using procedures set forth in the literature (e.g., *Polymer Preprints,* 39(1), p. 530 (1998)) in tetrahydrofuran/1,4-dioxane (2:1 v/v, 36 mL) was added 10% solution of platinum-1,3-divinyl-1,1,3,3-tetramethyldisiloxane complex in xylenes (0.01 mL) and the solution was heated 15 hours at 60° C. The solvents were removed from the cooled solution at reduced pressure and the crude product was purified via column chromatography (0-50% dichloromethane/pentane, silica gel, 5×5 cm) to provide a product as a colorless oil (3.95 g, 66%): $^1$H NMR (CDCl$^3$, 400 MHz) δ 7.15 (d, J=8 Hz, 4 H), 7.00 (d, J.=8 Hz, 4 H), 2.60 (t, J=8 Hz, 4 H), 1.66-1.60 (m, 4 H), 0.57 (t, J=8 Hz, 4 H), 0.07 (s, approximately 63H).

EXAMPLES 2-6

Various proportions of 3-(4-[trifluorovinyloxy]phenyl)propyl terminated poly(dimethylsiloxane) ($T_2D_8$) of Example 1 and 1,1,1-tris(4-[trifluorovinyloxy]phenyl)ethane ($T_3$) (crosslinker) obtained from Oakwood Products, Inc., (West Columbia, S.C.) were dissolved with gentle heating and stirring and each of the warm solutions was clamped between silanized glass plates with a Teflon tape spacer. Each of the glass plates containing the solution was heated for 20 hours at 195° C. under a nitrogen atmosphere. The cooled, transparent materials ranged from an organic soluble (i.e., dichloromethane), viscous oil (0% $T_3$) to a brittle, insoluble film (100% $T_3$). The properties of the polymers of examples 2-6 were determined to demonstrate modified mechanical properties as a function of crosslinking density. These results are set forth below in Table 1.

TABLE 1

| | Example | | | | |
|---|---|---|---|---|---|
| | 2 | 3 | 4 | 5 | 6 |
| $T_2D_8/T_3$ (w/w) | 0/100[a] | 25/75 | 50/50 | 75/25[b] | 100/0[c] |
| Modulus (g/mm$^2$) | — | 4962(211) | 3692(85) | — | — |
| Elongation (%) | — | 66(7) | 72(2) | — | — |
| Tensile Strength (g/mm$^2$) | — | 4091(415) | 785(44) | — | — |
| Dk | 20.5 | — | 70.3 | — | — |
| Refractive Index | 1.516 | — | 1.515 | — | — |

Numbers in parenthesis are standard deviation for last digits
[a]Sample shattered;
[b]sample tore;
[c]soluble, viscous oil

EXAMPLES 7-9

Poly(perfluorocyclobutane) with
4-(trifluorovinyloxy)benzoic acid as Wetting Agent Various proportions of 4-(trifluorovinyloxy)benzoic acid (TA) prepared from 1-bromo-4-(trifluorovinyloxy)benzene obtained from Oakwood Products, Inc. (West Columbia, S.C.) using procedures set forth in the literature (e.g., *Polymer Preprints,* 43(1), p. 487 (2002)), 3-(4-[trifluorovinyloxy]phenyl)propyl terminated poly(dimethylsiloxane) ($T_2D8$) of Example 1 and 1,1,1-(4-[trifluorovinyloxy]phenyl)ethane ($T_3$) were dissolved with stirring and gentle heat. The weight ratio of $T_2D_8$ to $T_3$ was held constant at 50:50 for all samples and the amount of TA was varied. The warm solution was clamped between silanized glass plates using Teflon tape spacer and heated under a nitrogen atmosphere at approximately 195° C. for 20 hours. The cooled, transparent, tack-free films were removed from the glass plates and further analyzed. Equilibrium water uptake was measured by measuring mass increase of film after soaking in deionized water (DI) up to 67 hour. Multiple static contact angle (SCA) measurements were conducted and reported. These results are set forth below in Table 2.

TABLE 2

Wetting properties of $T_2D_8/T_3$ films with TA wetting agent

| | Example | | |
|---|---|---|---|
| | 7 | 8 | 9 |
| TA (w/w %) | 0 | 3.4 | 8.7 |
| SCA (°) | 104(1) | 91(2) | 95(2) |
| Water (w/w %) | 0.0 | 1.8 | 2.2 |

Number in parenthesis represents standard deviation for last digit
The observed decrease in contact angle and increase in water content indicates increased surface wettability/hydrophilicity.

The observed decrease in contact angle and increase in water content indicates increased surface wettability/hydrophilicity.

EXAMPLE 10

Figure 5:
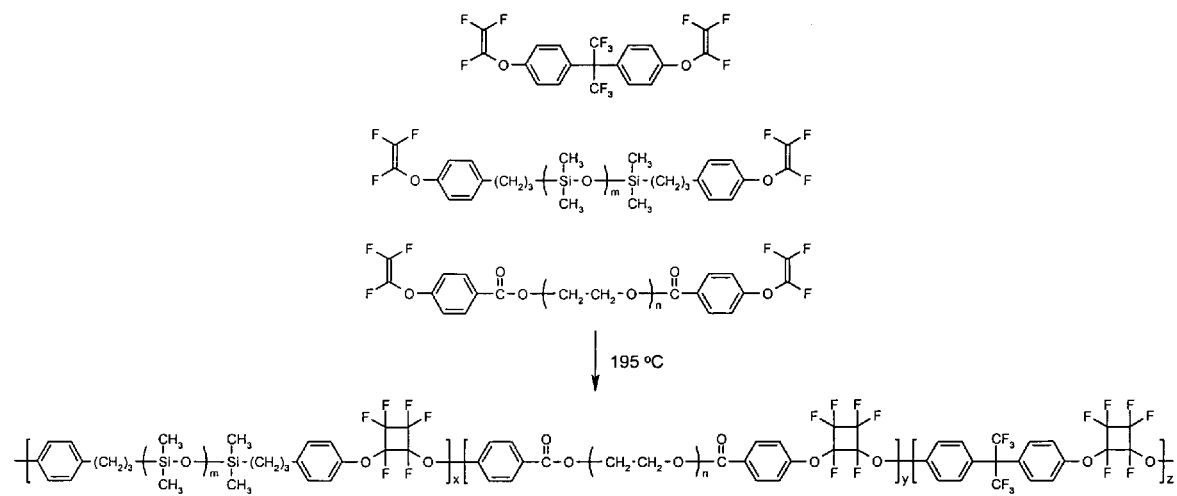
FIG. 5 illustrates the general reaction scheme of Example 10.

Copolymerization of T End-Capped poly(alkyl ether), poly(siloxane), and poly(PFCB) Prepolymers A monomeric mixture was prepared by dissolving 0.42 g of 4-(trifluorovinyloxy)benzoate terminated poly(ethylene glycol) (1) having a $M_n$ of 1006, a weight average molecular weight ($M_w$) of 1234 and a PD of 1.23, 3-(4-[trifluorovinyloxy]phenyl)propyl terminated poly(dimethylsiloxane) (2) of Example 1, and 0.43 g (1.11 mmol) of 2,2-bis(4-[trifluorovinyloxy]phenyl)-1,1,1,3,3,3-hexafluoropropane (3), with stirring and gentle heating. The warm solution (insoluble at ambient temperature) was clamped between silanized glass plates with a Teflon tape spacer and heated at 195° C. for 40 hours under nitrogen purge to afford a viscous, transparent oil (1.28 g, 100%); SEC (THF, PS standards). The reaction scheme of this example is generally set forth in FIG. 5 wherein m and n and x, y, and z are such that the copolymer has a $M_n$=3641, $M_w$=14664, and PD=4.03. The weight average molecular weight ($M_w$) was measured at various points during curing. These results are set forth below in Table 3.

TABLE 3

| Cure time | Weight average molecular weight (g/mol) | | | |
|---|---|---|---|---|
| (h) | 1 | 2 | 3 | Copolymer |
| 0 | 1234 | 2054 | N/A | N/A |
| 20 | 4993 | 8478 | 4133 | 6836 |
| 40 | 7668 | 15914 | 7498 | 14664 |

EXAMPLE 11

Synthesis of End-Capped poly(ethylene oxide) (Prepolymer 1)

A solution of 4-(trifluorovinyloxy)benzoyl chloride (1.85 g, 7.8 mmol) prepared from 1-bromo-4-(trifluorovinyloxy)benzene obtained from Oakwood Products, Inc. (West Columbia, S.C.) using procedures set forth in the literature (e.g., *Polymer Preprints,* 43(1), p. 487 (2002)) in tetrahydrofuran (5 mL) was treated with a solution of poly(ethylene oxide) having a $M_n$ of 300 (0.78 g, 2.6 mmol) and triethylamine (1.21 mL, 8.7 mmol) in tetrahydrofuran (5 mL) dropwise under inert atmosphere. After 15 hours at ambient temperature, the reaction mixture was diluted in dichloromethane (30 mL), washed with $NaHCO_3$(aq) (0.25 M, 1×25 mL), dried over $Na_2SO_4$, filtered, and solvents were removed under reduced pressure. The crude oil was purified by column chromatography (3×3 cm, silica gel, 0-50% dichloromethane/pentane) and solvents removed under reduced pressure to afford the product as a viscous oil (0.42 g, 23%): $^1$H NMR ($CDCl_3$, 400 MHz): δ 8.06 (d, 4 H, J=8 Hz), 7.11 (d, 4 H, J=8 Hz), 4.48 (br, 4 H), 3.79 (br, 4 H), 3.61 (br, 22.3 H); SEC (THF, PS standards): $M_n$=1006 g/mol, $M_w$=1234 g/mol, and a PD 1.23. This reaction is generally shown below in Scheme 1.

Scheme 1

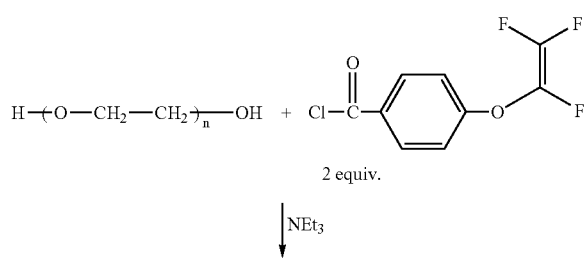

-continued

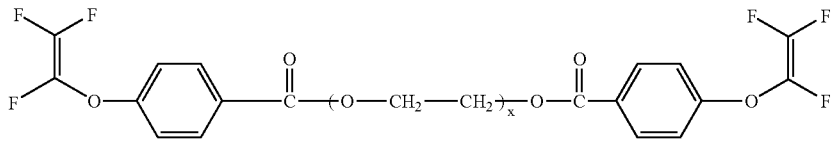

wherein the average value of x is approximately 7.

EXAMPLE 12

Synthesis of End-Capped poly(ethylene oxide-block-propylene oxide-block-ethylene oxide) (Prepolymer 2)

Polyoxamer 108 supplied as Pluronic F38 (4700 g/mol, 3.45 g), obtained from BASF Co. (Florham Park, N.J.) was reacted using substantially the same procedure described in Example 11 to afford the product as a solid (2.01 g, 54%): $M_n$=9637 g/mol, $M_w$=8761 g/mol, PD=1.10; $^1$H NMR (CDCl$_3$, 400 MHz); δ 8.08 (d, J=8 Hz, 4H), 7.13 (d, J=8 Hz, 4H), 4.54 (t, J=5 Hz, 4H), 3.82-3.37 (m, 530 H), 1.15-1.11 (m, 60 H). The final product is represented by the following formula:

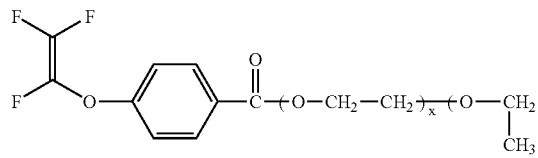

wherein x is y and z are such that the product has a $M_n$=9637 g/mol, $M_w$=8761 g/mol, and PD=1.1.

EXAMPLE 13

Synthesis of End-capped poly(perfluoroalkyl ether) (Prepolymer 3)

Fomblin Z DOL 2000 (a hydroxy terminated poly(perfluoroethylene containing glycol)) (2000 g/mol) obtained from Solvay Solexis (Thorofare, N.J.) was reacted using substantially the same procedure described in Example 11 except using dichloromethane instead of tetrahydrofuran as solvent to afford the product as a viscous oil (0.58 g, 17%): GPC (THF, PS standards): $M_n$=1604 g/mol, $M_w$=1656 g/mol, PD=1.05 g/mol; $^1$H NMR (CDCl$_3$, 400 MHz); δ 8.08 (d, J=8 Hz, 4 H), 7.15 (d, J=8 Hz, 4H), 4.67 (m, 4.70-4.64, 4H). The final product is represented by the following formula:

wherein m and n are such that the product has a $M_n$=1604, $M_w$=1656 g/mol, and PD=1.05.

EXAMPLE 14

Polymerization of Prepolymers 1-3

Samples of materials from Examples 11-13 were clamped between silanized glass plates with Teflon spacers and heated under nitrogen atmosphere at 195° C. for various times. In each case the isolated products were oils of varied viscosities. The linear polymers were dissolved in tetrahydrofuran (5 mg/mL) and analyzed via GPC (relative to PS standards) to demonstrate increase in molecular weight as a function of thermal cure time. The molecular weight analysis of the polymerized products are set forth below in Table 4.

TABLE 4

Molecular Weight Analysis of Thermal Trifluorovinylarylether end-capped Poly(alkyl ether) Polymerization at 195° C. as Determined by SEC

| | Prepolymer 1 | | Prepolymer 2 | | Prepolymer 3 | |
|---|---|---|---|---|---|---|
| Cure time (h) | $M_n$ (g/mol) | PD | $M_n$ (g/mol) | PD | $M_n$ (g/mol) | PD |
| 0 | 1006 | 1.23 | 9637 | 1.10 | 1604 | 1.05 |
| 20 | 2123 | 2.35 | 13205 | 1.43 | 2815 | 1.45 |
| 40 | 2945 | 2.60 | 19529 | 1.82 | 4707 | 1.71 |

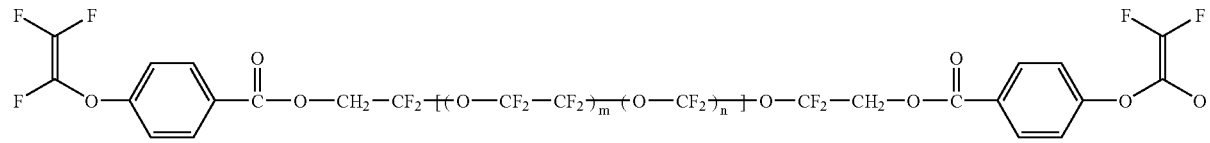

EXAMPLE 15

Synthesis of 2,4,6,8,10-pentamethyl-2,4,6,8,10-penta(3-[4-trifluorovinyloxyphenyl]propyl)cyclopentasiloxane (cyclo-(TD)$_5$)

Figure 2:
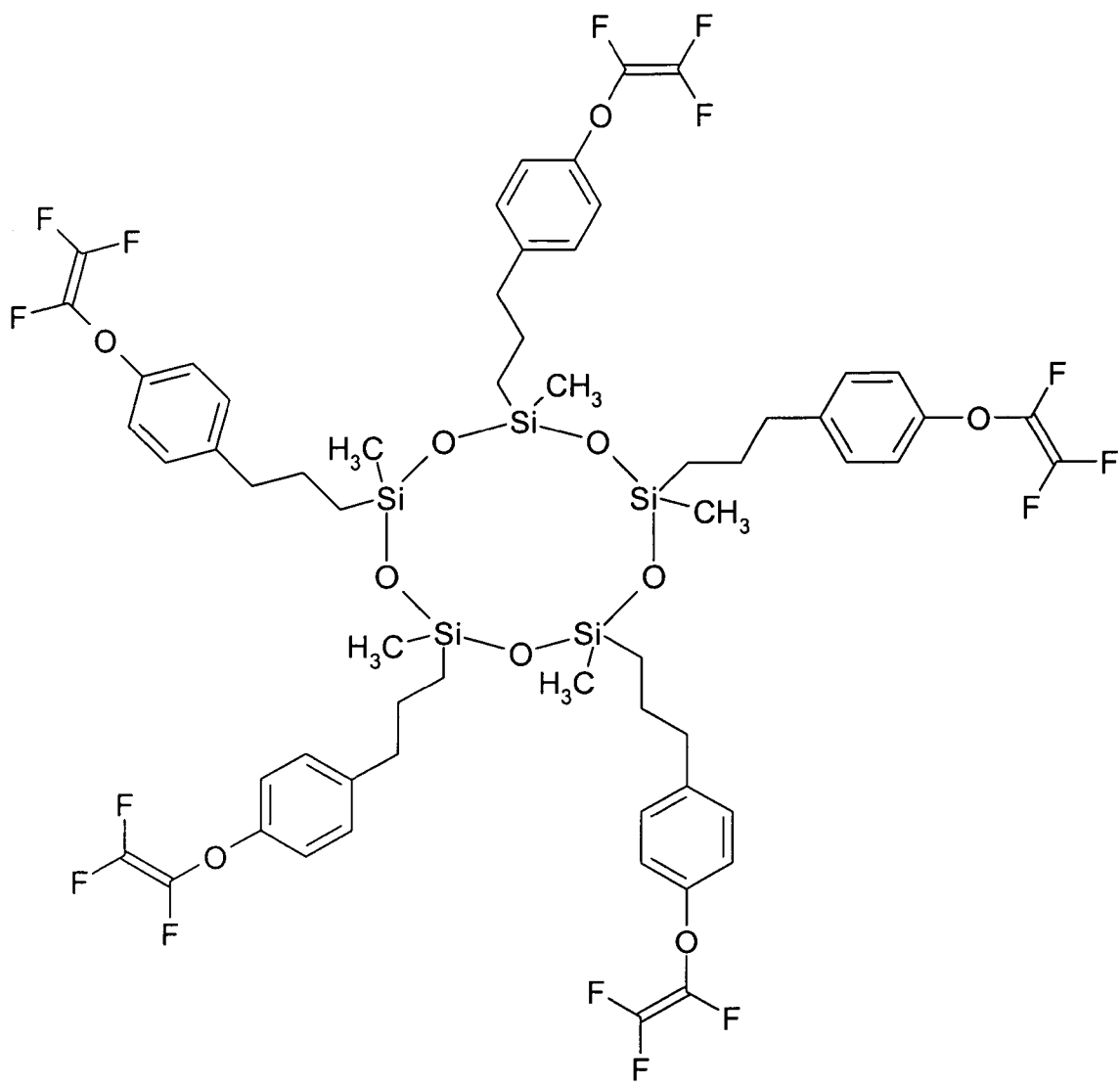
FIG. 2 is a polysiloxane containing cyclic monomer which can be employed in the manufacture of a biomedical device of the present invention.
Figure 3:
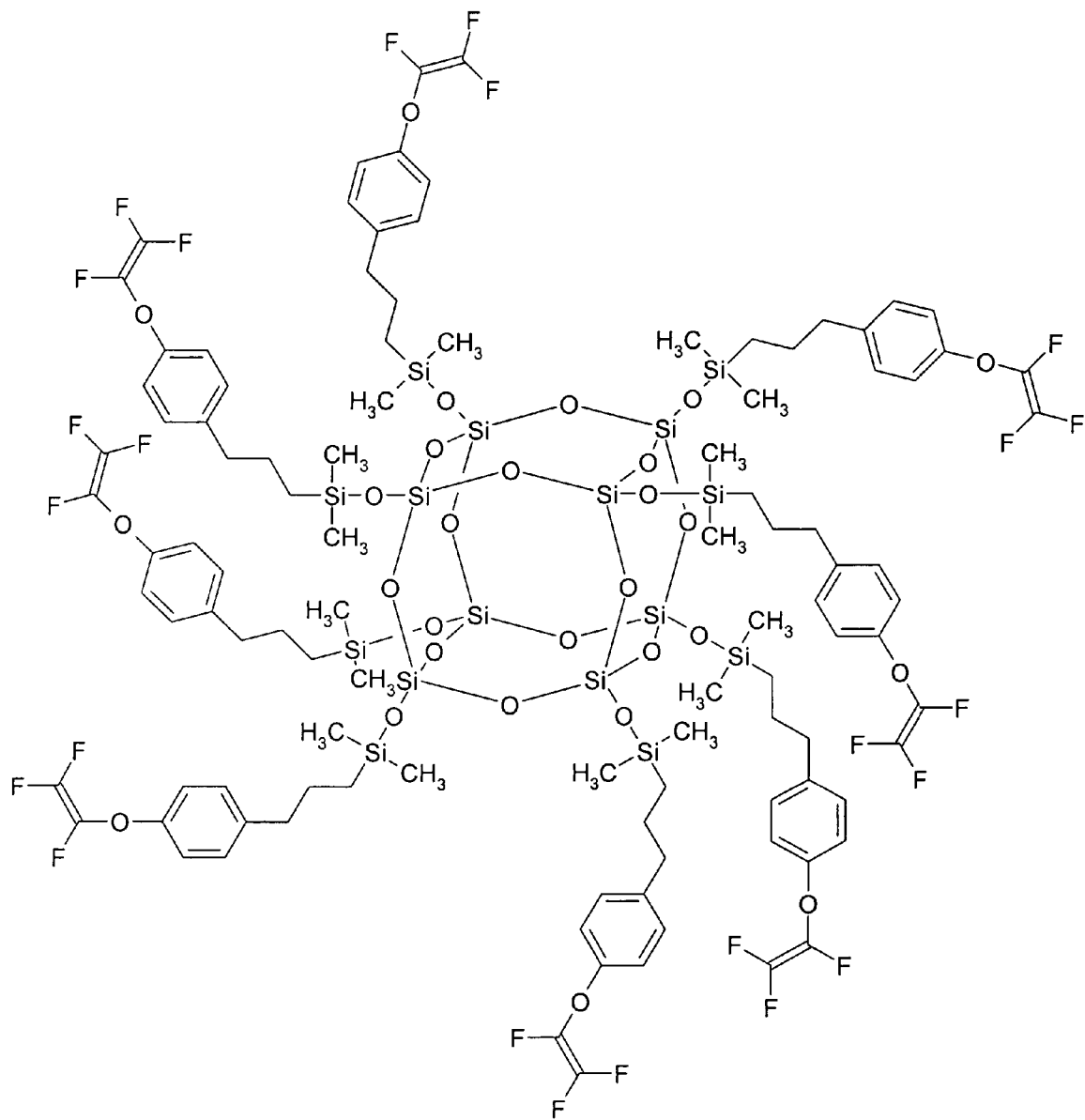
FIG. 3 is a polysiloxane containing polycyclic monomer which can be employed in the manufacture of a biomedical device of the present invention.

A solution of 2,4,6,8,10-pentamethylcyclopentasiloxane (0.34 g, 1.13 mmol) and 4-(trifluorovinyloxy}allylbenzene (1.83 g, 8.55 mmol) in 2:1 tetrahydrofuran/1,4-dioxane (17 mL) was treated with platinum-1,3-divinyl-1,1,3,3-tetramethyldisiloxane complex in xylenes (0.09 mL) and heated at 60° C. for 15 hours. The cooled solution was concentrated under reduced pressure and purified via column chromatography (0-50% ethyl ether/pentane, silica gel, 3×10 cm) to afford the product as a viscous oil (57 mg, 4%): $^1$H NMR (CDCl$_3$, 400 MHz) δ 7.09 (br, 2 H), 6.99 (br, 2 H), 2.55 (br, 2 H), 1.59 (br, 2 H), 0.5 (br, 2 H), 0.02 (br, 3H). The final product is shown in FIG. 2.

EXAMPLE 16

Homopolymerization of cyclo-(TD)$_5$

The product prepared in Example 15 was clamped between two silanized glass plates with Teflon tape spacer and heated at 195° C. under a nitrogen purge for 20 hours to result in a transparent, insoluble, tack-free film: DSC, T$_g$ 94° C.

EXAMPLE 17

Crosslinking of 3-(4-[trifluorovinyloxy]phenyl)propyl terminated poly(dimethylsiloxane) (T$_2$D8) using cyclo-(TD)$_5$ The product of Example 15 (25 parts) and 3-(4-[trifluorovinyloxy]phenyl)propyl terminated poly(dimethylsiloxane) of Example 1 (75 parts) were dissolved with gentle heat and agitation and polymerized as in Example 16 to result in a transparent, insoluble, tack-free film: DSC, No transitions were observed between −100 to 300° C.

EXAMPLE 18

Thermal Cast Molding of poly(perfluorocyclobutane) Films 1,1,1-Tris(4-[trifluorovinyloxy]phenyl)ethane (2.00 g, 3.66 mmol), obtained from Oakwood Products, Inc. was melted with gentle heating and clamped between glass plates with Teflon® tape spacers of varied thicknesses. The assemblies were sealed in a heating oven with a constant N$_2$ purge and heated for 20 hours at 195° C. The cooled films were then removed from the plates to yield a transparent, colorless, glassy film. The films were further cut into wafers for oxygen permeability and refractive index determination: The oxygen permeability for the wafer was a Dk of 20.5 Barrers, and the refractive index was 1.516.

EXAMPLE 19

Thermal Cast Molding of poly(perfluorocyclobutane) Button 1,1,1-Tris(4-[trifluorovinyloxy]phenyl)ethane (2 g, 3.66 mmol), obtained from Oakwood Products, Inc. was added to a flat-bottomed, 15 mm diameter glass test tube. The vessel was sealed in a heating oven with a constant N$_2$ purge and heated for 68 hours at 155° C. The cooled vessel was removed from the oven and test tube to yield a transparent, colorless, glassy button for lathing into a Rigid, Gas-Permeable (RGP) contact lens.

EXAMPLE 20

Machining of Lens From poly(perfluorocyclobutane) Button

The poly(perfluorocyclobutane) button prepared in Example 19 was machine lathed using processes and procedures well known in the art on a DAC material table using a feed rate of 2.5 (cut amount 0.3 mm) for rough lathing and finished using a feed rate of 1.0 (cut amount 0.05 mm) to afford a transparent, rigid ophthalmic lens of a quality comparable to current commercial gas-permeable lenses.

It will be understood that various modifications maybe made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. An ophthalmic lens formed from a polymerization product of a monomeric mixture comprising one or more monomers having at least two dimerizable perfluorovinyl groups.

2. The ophthalmic lens of claim 1, wherein the monomeric mixture comprises one or more monomers having at least two dimerizable perfluorovinyl ether groups.

3. The ophthalmic lens of claim 1, wherein the monomeric mixture comprises one or more monomers having at least two dimerizable perfluorovinyl aromatic ether groups.

4. The ophthalmic lens of claim 1, wherein the monomeric mixture comprises one or more monomers having at least two dimerizable perfluorovinyl groups of the general formula

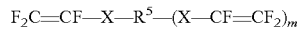

$$F_2C=CF-X-R^5-(X-CF=CF_2)_m$$

wherein R$^5$ represents one or more inertly substituted groups; X is independently a group which links the R$^5$ group and the trifluorovinyl group and m is an integer of 1 to about 1000.

5. The ophthalmic lens of claim 4, wherein R$^5$ comprises a substituted or unsubstituted cyclic or polycyclic containing group or a substituted or unsubstituted cyclic or polycyclic siloxane containing group, X is independently a bond, an oxygen atom, a sulfur atom, a carboxylic or thiocarboxylic ester group, an amide group, a sulfone, a sulfoxide, a carbonate, a carbamate, a perfluoroalkylene, a perfluoroalkylene ether, an alkylene, an acetylene, a phosphine, a carbonyl or thiocarbonyl group; seleno; telluro; nitrido; a silanediyl group, a trisilanediyl group, a tetrasilanetetrayl group, a siloxanediyl group, a disiloxanediyl group, a trisiloxyldiyl group, a trisilazanyl group, a silythio group, or a boranediyl group and m is from 1 to about 10.

6. The ophthalmic lens of claim 4, wherein each X is O, R$^5$ selected from the group consisting of

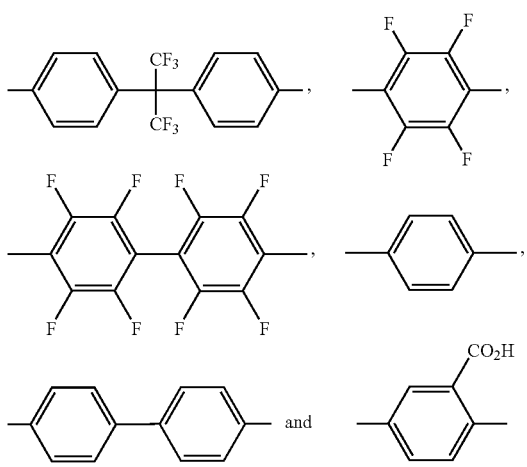

and wherein each O atom may independently be bonded to the aromatic group either ortho, meta and/or para with respect one another and m is 1 to about 5.

7. The ophthalmic lens of claim 1, wherein the monomer mixture comprises one or monomers of the general formula

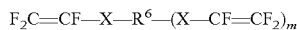

wherein $R^6$ is one or more substituted or unsubstituted $C_3$-$C_{25}$ cycloalkyl groups optionally containing one or more heteroatoms; each X is independently a group which links the $R^6$ group and the trifluorovinyl group; and m is an integer of 1 to about 1000.

8. The ophthalmic lens of claim 7, wherein each X is O, $R^6$ is selected from the group consisting of

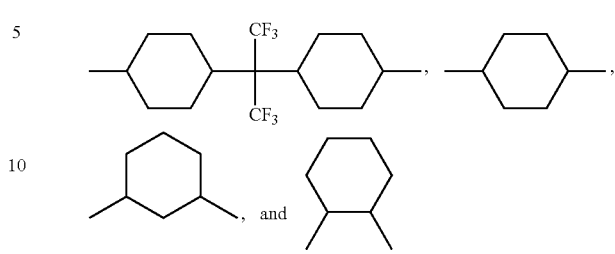

and m is 1 to about 10.

9. The ophthalmic lens of claim 4, wherein the polymerization product is a thermal polymerization product.

10. The ophthalmic lens of claim 1, wherein the ophthalmic lens is a contact lens.

11. The ophthalmic lens of claim 10, wherein the contact lens is a rigid gas permeable lens.

12. An ophthalmic lens formed from a polymerization product of a monomeric mixture comprising one or more polysiloxane containing monomers having at least two dimerizable perfluorovinyl groups.

13. The ophthalmic lens of claim 12, wherein the polysiloxane containing monomer is a polysiloxane containing cyclic monomer.

14. The ophthalmic lens of claim 12, wherein the polysiloxane containing monomer is a polysiloxane containing polycyclic monomer.

* * * * *